(12) United States Patent
Sugahara et al.

(10) Patent No.: US 11,400,122 B2
(45) Date of Patent: Aug. 2, 2022

(54) COMPOSITION FOR ALLEVIATING MENTAL HEALTH DISORDER

(71) Applicant: MORINAGA MILK INDUSTRY CO., LTD., Tokyo (JP)

(72) Inventors: Hirosuke Sugahara, Kanagawa (JP); Kanetada Shimizu, Kanagawa (JP); Toshitaka Odamaki, Kanagawa (JP); Yeong Yeh Lee, Kubang Kerian Kelantan (MY)

(73) Assignee: MORINAGA MILK INDUSTRY CO., LTD., Tokyo (JP)

(*) Notice: Subject to any disclaimer, the term of this patent is extended or adjusted under 35 U.S.C. 154(b) by 269 days.

(21) Appl. No.: 16/487,951

(22) PCT Filed: Feb. 22, 2018

(86) PCT No.: PCT/JP2018/006489
§ 371 (c)(1),
(2) Date: Aug. 22, 2019

(87) PCT Pub. No.: WO2018/155565
PCT Pub. Date: Aug. 3, 2018

(65) Prior Publication Data
US 2020/0038460 A1    Feb. 6, 2020

(30) Foreign Application Priority Data
Feb. 24, 2017 (JP) .............................. JP2017-033822

(51) Int. Cl.
*A61K 35/745* (2015.01)
*A61P 25/00* (2006.01)

(52) U.S. Cl.
CPC ............ *A61K 35/745* (2013.01); *A61P 25/00* (2018.01)

(58) Field of Classification Search
None
See application file for complete search history.

(56) References Cited

U.S. PATENT DOCUMENTS

| 2004/0265279 A1 | 12/2004 | Dinan et al. |
| 2013/0150306 A1 | 6/2013 | Wittke |

FOREIGN PATENT DOCUMENTS

| JP | 2006-525313 A | 11/2006 | |
| JP | 2010-209022 A | 9/2010 | |
| JP | 2012-223134 A | 11/2012 | |
| JP | 2013-119546 A | 6/2013 | |
| JP | 2016-503025 A | 2/2016 | |
| JP | 2016-199491 A | 12/2016 | |
| WO | WO-2017037089 A1 * | 3/2017 | ........... A23L 33/135 |

OTHER PUBLICATIONS

Desbonnet, L., et al., "The probiotic Bifidobacteria infantis: An assessment of potential antidepressant properties in the rat," J. Psych. Res. 2009;43:164-174.
Abe, F., et al., "Safety evaluation of probiotic bifidobacteria by analysis of mucin degradation activity and translocation ability," Anaerobe 2010;16:131-136.
Rao, A. V., et al., "A randomized, double-blind, placebo-controlled pilot study of a probiotic in emotional symptoms of chronic fatigue syndrome," Gut Pathogens 2009, 1:6, 2009, 6 pp.
International Search Report for PCT Patent App. No. PCT/JP2018/006489 (dated Apr. 3, 2018).
International Preliminary Report On Patentability for PCT Patent App. No. PCT/JP2018/006489 (dated Sep. 6, 2019).
Extended European Search Report for European Patent App. No. 18756733.4 (dated Nov. 20, 2020).
Giannetti, E., et al., "A Mixture of 3 Bifidobacteria Decreases Abdominal Pain and Improves the Quality of Life in Children With Irritable Bowel Syndrome," J. Clin. Gastroenterol. 2017;51(1):e5-e10.
Database GNPD [Online] Mintel; Dec. 29, 2016, anonymous: "Probiotic Cultures," Database accession No. 4459519, pp. 1-4.
Abe, F., et al., "Stability of bifidobacteria in powdered formula," Int. J. Food Sci. Technol. 2009;44:718-724.
Desbonnet, L., et al., "Effects of the Probiotic Bifidobacterium Infantis in the Maternal Separation Model of Depression," Neurosci 2010;170(4):1179-1188.
Ma, Z. F., et al., "Bifidobacterium infantis M-63 improves mental health in victims with irritable bowel syndrome developed after a major flood disaster," Beneficial Microbes 2019;10(2):111-120.
Decision of Refusal from Japanese Patent App. No. 2019-501419 (dated Apr. 26, 2022).
"Mental Health and Work: Misconceptions and Realities: How Should Labor Market Address Mental Illness?" published by Akashi Shoten, 2013, pp. 19-29, with partial English language translation included, complete English language translation available for viewing only at https://read.oecd-ilibrary.org/social-issues-migration-health/mental-health-and-work_9789264124523-en#page5.

\* cited by examiner

*Primary Examiner* — Michelle F. Paguio Frising
(74) *Attorney, Agent, or Firm* — Cermak Nakajima & McGowan LLP; Shelly Guest Cermak

(57) ABSTRACT

An object of the present invention is to provide an agent for improving a mental health disfunction or a composition for improving a mental health disfunction, and a food or drink composition for improving a mental health disfunction which are effective for improving a mental health disfunction, which are highly safe, and which can be continuously ingested on a daily basis, and this object is achieved by an agent for improving a mental health disfunction or a composition for improving a mental health disfunction, or a food or drink composition for improving a mental health disfunction, each comprising as an active ingredient a bacterium belonging to *Bifidobacterium longum* subsp. *infantis*.

3 Claims, 8 Drawing Sheets
Specification includes a Sequence Listing.

COMPOSITION FOR ALLEVIATING MENTAL HEALTH DISORDER

This application is a national phase filing under 35 U.S.C. 371 of, and claims priority to, International Application No. PCT/JP2018/006489, filed Feb. 22, 2018, and claims priority therethrough under 35 U.S.C. § 119 to Japanese Patent Application No. 2017-033822, filed Feb. 24, 2017, the entireties of which are incorporated by reference herein. Also, the Sequence Listing filed electronically herewith is hereby incorporated by reference (File name: 2019-08-22T_216-017_Seq_List; File size: 1000 Bytes; Date recorded: Aug. 21, 2019).

TECHNICAL FIELD

The present invention relates to an agent for improving a mental health disfunction or a composition for improving a mental health disfunction, and a food or drink composition for improving a mental health disfunction.

BACKGROUND ART

In recent years, even if people living in the modern society do not eventually acquire diseases such as mental disorders due to various stresses caused by diversification of living environments and working environments, complication of human relationships and the like, people often have rather poor mental health, namely mental wellness or mental hygiene. Also, because of an increase of natural disasters, there have been an increasing number of cases where victims of the natural disasters are forced to change their living environments, resulting in deterioration of their mental health conditions, and mental health disorders. When a person is in a state of such mental health disorders and it continues for a long period, this leads to poor physical health conditions or mental disorders in some cases. In cases where a mental disorder such as depression occurs, a long period of medication causing side effects is required in some cases. Thus, appropriate care is required for a mental health disfunction so that development of mental disorders does not occur. However, it is not appropriate to use chemically synthesized drugs such as tranquilizers having side effects for daily care of a mental health disfunction. Therefore, there is a demand for effective drugs or foods/drinks for improving a mental health disfunction which can be casually ingested on a daily basis and which do not show side effects at a stage before development of mental disorders such as depression preferably.

Regarding improvement of a mental health disfunction, Patent Document 1 discloses an agent for improving a psychological state comprising an iso-alpha acid or a reduced iso-alpha acid as an active ingredient, as the agent for improving psychological state which improves mood and alleviates psychological tension to thereby increase comfort.

Patent Document 2 discloses an agent for improving mood state characterized in that it comprises a turmeric extract, as the agent for improving mood state which alleviates depressed mood that occurs as a phenomenon caused by complex combination of physical exhaustion and psychological stresses.

On the other hand, bifidobacteria and lactic acid bacteria as probiotics have been known to have useful effects such as an intestinal function-controlling action. Recently, the intestinal environment has been known to be involved in signaling from the intestine to the brain, brain-gut interaction, and probiotics have been known to influence also brain functions through interactions with the intestinal flora. For example, Non-patent Document 1 discloses that anxiety symptoms in a patient with chronic fatigue syndrome, CFS, were improved by ingestion of *Lactobacillus casei* Shirota strain. Further, Patent Document 3 discloses a therapeutic method for depression or a disease characterized by hypothalamus-hypophysis-adrenal axis hypersensitivity by administration of a probiotic such as a *Lactobacillus* bacterium or a *Bifidobacterium* bacterium.

Thus, effectiveness of ingestion of probiotic bacterial cells on mental diseases such as depression has already been reported, and probiotics have been known to show different physiological actions depending on the bacterial type. Moreover, it has not been known that *Bifidobacterium longum* subsp. *infantis* BCCM LMG23728 is useful for improvement of a mental health disfunction.

PRIOR ART DOCUMENTS

Patent Documents

Patent Document 1: Japanese Patent Laid-open (kokai) No. 2010-209022
Patent Document 2: Japanese Patent Laid-open (kokai) No. 2016-199491
Patent Document 3: Japanese Patent Laid-open (kokai) No. 2006-525313

Non-Patent Documents

Non-patent Document 1: A Venket Rao et al., Gut Pathog., 2009, 1: 6

SUMMARY OF THE INVENTION

Problems to be Solved by the Invention

The present invention was made under the above circumstances. An object of the present invention is to provide an agent for improving a mental health disfunction or a composition for improving a mental health disfunction, and a food or drink composition for improving a mental health disfunction, which are effective for improving a mental health disfunction, which are highly safe, and which can be continuously ingested on a daily basis.

Means for Solving the Problems

As a result of intensive study to solve the problem, the present inventors discovered that a bacterium belonging to *Bifidobacterium longum* subsp. *infantis* has an action that improves a mental health disfunction through a change in the intestinal flora, thereby completing the present invention.

That is, the present invention is an agent for improving a mental health disfunction or a composition for improving a mental health disfunction comprising as an active ingredient a bacterium belonging to *Bifidobacterium longum* subsp. *infantis*.

In a preferred mode of the agent for improving a mental health disfunction or the composition for improving a mental health disfunction, the bacterium is *Bifidobacterium longum* subsp. *infantis* BCCM LMG23728 or *Bifidobacterium longum* subsp. *infantis* M-63 (NITE BP-02623).

Further, in a preferred mode of the agent for improving a mental health disfunction or the composition for improving a mental health disfunction, the mental health disfunction is evaluated according to SF-36.

Further, in a preferred mode of the agent for improving a mental health disfunction or the composition for improving a mental health disfunction, the mental health disfunction is a state with a low score(s) of mental health (MH) and/or mental component summary (MCS).

Further, the present invention provides a food or drink composition for improving a mental health disfunction comprising as an active ingredient a bacterium belonging to *Bifidobacterium longum* subsp. *infantis*.

In a preferred mode of the food or drink composition for improving a mental health disfunction, the bacterium is *Bifidobacterium longum* subsp. *infantis* BCCM LMG23728 or *Bifidobacterium longum* subsp. *infantis* M-63 (NITE BP-02623).

Effect of the Invention

According to the present invention, means for effectively improving a mental health disfunction can be provided. More specifically, an agent for improving a mental health disfunction or a composition for improving a mental health disfunction, and a food or drink composition for improving a mental health disfunction, which are effective for improvement of a mental health disfunction, which are highly safe, and which can be continuously ingested on a daily basis, can be provided.

The bacterium belonging to *Bifidobacterium longum* subsp. *infantis* used in the present invention is originally present in the intestinal flora of mammals, and is therefore highly safe to living bodies and free from concern about side effects, so that the bacterium is useful as a drug or a food or drink.

MODE FOR CARRYING OUT THE INVENTION

Figure 1:
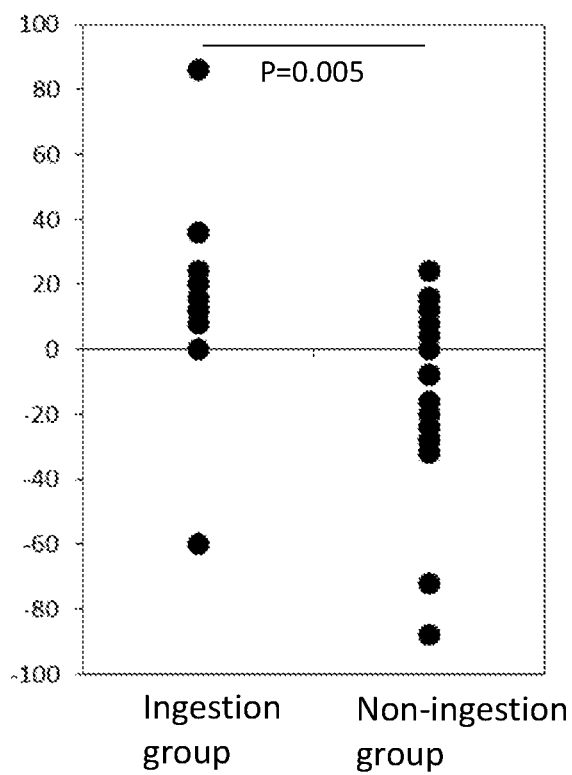
FIG. 1 shows a diagram illustrating changes in the "mental health, MH" score according to SF-36 for a group who ingested *Bifidobacterium longum* subsp. *infantis* BCCM LMG23728 and a group who did not ingest it.

Embodiments of the present invention are described below. However, the present invention is not limited to the following embodiments, and may be arbitrarily modified within the scope of the present invention.

The agent of the present invention for improving a mental health disfunction comprises as an active ingredient a bacterium belonging to *Bifidobacterium longum* subsp. *infantis*. It should be noted that, while the agent for improving a mental health disfunction of the present invention contains as an active ingredient the bacterium belonging to *Bifidobacterium longum* subsp. *infantis*, inclusion of other components is not prohibited. That is, the agent for improving a mental health disfunction of the present invention is equivalent to the composition for improving a mental health disfunction. Thus, another mode of the present invention is a composition for improving a mental health disfunction comprising as an active ingredient the bacterium belonging to *Bifidobacterium longum* subsp. *infantis*.

The "mental health" in the present invention is "a state of well-being in which every individual realizes his or her own potential, can cope with the normal stresses of life, can work productively and fruitfully, and is able to make a contribution to her or his community" as defined by World Health Organization, WHO, in 2007 and translated into Japanese.

The "mental health disfunction" in the present invention means a state where the above state is deteriorated in a subject. For example, the "mental health disfunction" is a nervous psychological state, depressed mood state, or melancholic mood state of the subject.

The "improvement of a mental health disfunction" in the present invention means that the "mental health disfunction" is improved, and also means that a state where the "mental health" is deteriorated is changed to a state where it is not deteriorated. Examples of such improvement include cases where a nervous psychological state, depressed mood state, or melancholic mood state of a subject is alleviated, improved, or resolved, and cases where the subject can be judged to have acquired a mild mood state or a pleasant mood state.

Whether or not the subject has a mental health disfunction and whether or not the mental health disfunction of the subject was improved may be subjectively judged by the subject himself, or may be objectively judged by a physician or the like. The evaluation is preferably objectively carried out by a psychological test or the like.

The subject to whom the present invention applies is a human with a mental health disfunction, or a human who requires improvement of a mental health disfunction, but which human is free of mental disorders and mental diseases. Whether or not the subject requires improvement of a mental health disfunction may be subjectively judged by the subject himself, or may be objectively judged by a physician or the like.

Examples of the mental disorders and the mental diseases include depression, bipolar disorder (manic-depressive psychosis), and schizophrenia. Among these, for example, whether or not a patient has depression can be diagnosed by, for example, Optical Topography (registered trademark) or a blood test. Thus, in the present invention, a human who is not diagnosed with depression by these tests can be the subject. In cases of a blood test, because a patient is diagnosed with depression when an ethanolamine phosphate concentration is 1.5 µM or less in a plasma, the subject to whom the present invention applies has an ethanolamine phosphate concentration in a plasma of preferably more than 1.5 µM, more preferably 2.0 µM or more, still more preferably 2.5 µM or more. On the other hand, although there is no upper limit of the concentration, it is preferably 5.0 µM or less, more preferably 4.0 µM or less, still more preferably 3.0 µM or less.

Also for other mental disorders and mental diseases, it can be diagnosed by known methods whether or not a patient has such disorders/diseases.

Thus, the agent of the present invention for improving a mental health disfunction or the composition of the present invention for improving a mental health disfunction preferably does not include those for therapeutic uses for the mental disorders and the mental diseases. The mental health disfunction improved by the present invention is, in the first place, different from the mental disorders and the mental diseases.

The subject to whom the present invention applies is preferably a victim of a natural disaster such as earthquakes, floods, and tsunamis. When a natural disaster occurs, a large number of victims are produced at one time, and the victims have a wide variety of mental health states, so that such victims need to be supported differently from ordinary patients with mental diseases.

Moreover, such victims are forced to cope with various stresses caused by, for example, physical trauma, damage to lands and buildings, and moving to temporary housing. Even in cases where the individual stresses are mild, combination of such stresses may lead to symptoms called the dripping faucet syndrome, which causes irritation, social withdrawal, anhedonia, and the like. Thus, the "subject" in the present invention is more preferably a human with the dripping faucet syndrome.

When the "mental health disfunction" in the present invention is evaluated based on an objective scale by a psychological test or the like, examples of the psychological test include SF-36 (MOS 36-Item Short-Form Health Survey). SF-36 is a registered trademark of Medical Outcomes Trust.

SF-36 is a scale for evaluation of health-related QOL (HRQOL) based on scores from 36 questions grouped into the following eight items: "Physical Functioning (PF)", "Role Physical (RP)", "Bodily Pain (BP)", "General Health Perception (GH)", "Vitality (VT)", "Social Functioning (SF)", "Role Emotional (RE)", and "Mental Health (MH)". The higher the scores in general, the better the QOL is evaluated to be. SF-36 is a scientific, reliable, and proper scale for measurement of health-related QOL. It was created in the US, and is now used worldwide. SF-36 categorizes the eight items into two groups, the physical component and the mental component, and QOL can be evaluated based on two components, the QOL summary score for the physical component (Physical Component Summary; PCS) and the QOL summary score for the mental component (Mental Component Summary; MCS) (The Journal of Japanese Society of Lumbar Spine Disorders, vol. 8 (1), pp. 38-43, 2002).

In the present description, when the "mental health (Mental Health; MH)" is mentioned, it is described as "mental health (Mental Health; MH)", "mental health (MH)", "mental health", "Mental Health", "MH", or the like. This also applies to other items.

When the "mental health disfunction" in the present invention is evaluated according to SF-36, it is preferably a state where the score(s) of "mental health (MH)" and/or "mental component summary (MCS)" is/are low. In such a case, the score of "mental health (MH)" is preferably 70 or less, more preferably 60 or less, still more preferably 50 or less. The score of "mental component summary (MCS)" is preferably 50 or less, more preferably 40 or less, still more preferably 30 or less.

When the "improvement of a mental health disfunction" in the present invention is evaluated according to SF-36, the mental health disfunction is evaluated as having been improved in cases where the score(s) of "mental health (MH)" and/or "mental component summary (MCS)" increased.

The mental health disfunction to be improved in the present invention is different from mental diseases such as depression, bipolar disorder (manic-depressive psychosis), and schizophrenia. In cases where a patient is with these mental diseases, the scores of SF-36 other than "mental health (MH)" and "mental component summary (MCS)" are also generally low. For example, inpatients with these mental diseases, the score of "physical functioning (PF)" is preferably 70 or less, more preferably 60 or less. The score of "role physical (RP)" is preferably 70 or less, more preferably 60 or less. The score of "bodily pain (BP)" is preferably 80 or less, more preferably 70 or less. The score of "general health perception (GH)" is preferably 60 or less, more preferably 50 or less. The score of "vitality (VT)" is preferably 60 or less, more preferably or less. The score of "social functioning (SF)" is preferably 80 or less, more preferably 70 or less. The score of "role emotional (RE)" is preferably 80 or less, more preferably 70 or less. The score of "physical component summary (PCS)" is preferably 50 or less, more preferably 40 or less.

As the bacterium belonging to *Bifidobacterium longum* subsp. *infantis* used in the present invention, one type or two or more types of known bacteria belonging to *Bifidobacterium longum* subsp. *infantis* may be arbitrarily selected and used as long as the effect of the present invention is not deteriorated. In particular, in a preferred mode of the present invention, the bacterium is *Bifidobacterium longum* subsp. *infantis* BCCM LMG23728. The *Bifidobacterium longum* subsp. *infantis* used in the present invention may be simply referred to as *Bifidobacterium infantis*.

*Bifidobacterium longum* subsp. *infantis* BCCM LMG23728 can be obtained from Belgian Coordinated Collections of Microorganisms (BCCM) (address: Rue de la Science (Wetenschapsstraat) 8, B-1000 Brussels, Belgium), which is a preservation organization in Belgium.

*Bifidobacterium longum* subsp. *infantis* BCCM LMG23728 is the same bacterium as *Bifidobacterium longum* subsp. *infantis* M-63 (NITE BP-02623), and either bacterium may be used in the preferred mode. *Bifidobacterium longum* subsp. *infantis* M-63 (NITE BP-02623) has been deposited with Patent Microorganisms Depositary, National Institute of Technology and Evaluation (Room 122, 2-5-8 Kazusakamatari, Kisarazu-shi, Chiba, 292-0818

Japan) under the accession No. NITE BP-02623 as of Jan. 26, 2018 as international deposition in accordance with the Budapest Treaty.

In the present description, the "same bacterium" is a bacterium which belongs to the same genus or same species as the deposited bacterium, whose base sequence of the 16S rRNA gene has a homology of 98% or more, preferably 99% or more, more preferably 100% to the base sequence of the 16S rRNA gene of the deposited bacterium, and which has the same bacteriological characteristics as the deposited bacterium.

Further, the bacterium or the same bacterium as this bacterium may be a bacterium established from these bacteria by mutation treatment, genetic recombination, selection of a natural mutant strain, or the like as long as the effect of the present invention is not deteriorated.

The bacterium belonging to *Bifidobacterium longum* subsp. *infantis* in the present invention can be easily grown by culture.

The method of culturing the bacterium belonging to *Bifidobacterium longum* subsp. *infantis* in the present invention is not limited as long as the bacterium can be grown. A method ordinarily used for culture of the bacterium may be used, if necessary, after appropriate modification. The culture temperature may be, for example, 25 to 50° C., preferably 30 to 40° C. The culture is preferably carried out under anaerobic conditions, for example, under the flow of an anaerobic gas such as carbon dioxide gas.

The medium for culturing the bacterium belonging to *Bifidobacterium longum* subsp. *infantis* is not limited, and a medium ordinarily used for culture of the bacterium may be used, if necessary, after appropriate modification. Examples of carbon sources that may be used for the medium include sugars such as galactose, glucose, fructose, mannose, cellobiose, maltose, lactose, sucrose, trehalose, starch, starch hydrolysates, and waste molasses, which may be used according to the assimilability. Examples of nitrogen sources that may be used for the medium include ammonia; ammonium salts such as ammonium sulfate, ammonium chloride, and ammonium nitrate; and nitrates. Examples of inorganic salts that may be used for the medium include sodium chloride, potassium chloride, potassium phosphate, magnesium sulfate, calcium chloride, calcium nitrate, manganese chloride, and ferrous sulfate. Further, organic components such as peptone, soy powder, defatted soybean cake, meat extract, and yeast extract may be used for the medium. Further, as the medium, a prepared medium such as MRS medium may be preferably used.

As the bacterium belonging to *Bifidobacterium longum* subsp. *infantis* in the present invention, a culture product obtained after the culture may be used as it is or after dilution or concentration, or bacterial cells collected from the culture product may be used. The bacterium may be either a live bacterium or a dead bacterium, or may include both a live bacterium and a dead bacterium. The bacterium is preferably a live bacterium.

As long as the effect of the present invention is not deteriorated, an additional operation such as heating or freeze-drying may be carried out after the culture. The additional operation is preferably an operation that allows high survivability of live bacterial cells.

By ingestion of the agent for improving a mental health disfunction or the composition for improving a mental health disfunction of the present invention by the subject, the mental health disfunction of the subject can be improved. Because the bacterium belonging to *Bifidobacterium longum* subsp. *infantis* used as an active ingredient of the agent for improving a mental health disfunction or the composition for improving a mental health disfunction of the present invention has long been used in foods and agents, and because the bacterium is present as a good bacterium in the intestines of animals, the bacterium can be expected to be highly safe to living bodies. Thus, because side effects and dependence are unlikely to occur, the bacterium can be ingested continuously for a long period, and can be casually ingested by the subject. Because the agent for improving a mental health disfunction or the composition for improving a mental health disfunction of the present invention can be in the form of a drug or a food or drink that can be ingested on a daily basis, it can be used as a mental health disfunction-improving drug or a food or drink composition for improving a mental health disfunction.

<Drug>

The drug of the present invention for improving a mental health disfunction is not limited as long as it comprises a bacterium belonging to *Bifidobacterium longum* subsp. *infantis*. As the drug of the present invention improving a mental health disfunction, the bacterium belonging to *Bifidobacterium longum* subsp. *infantis* may be used as it is, or a formulation may be prepared by mixing it with a physiologically acceptable liquid or formulation carrier.

The dosage form of the drug of the present invention for improving a mental health disfunction is not limited. The drug may be prepared into, for example, a solid formulation such as a powder, granule, tablet, and capsule; a liquid formulation such as a solution, syrup, suspension, and emulsion; a suppository; or an ointment. For the formulation, a formulation carrier used for ordinary formulation may be used. The drug of the present invention for improving a mental health disfunction may also contain a component which is known or which will be found in the future having an effect of improving a mental health disfunction.

In the drug of the present invention for improving a mental health disfunction, the content of the bacterium belonging to *Bifidobacterium longum* subsp. *infantis* is not limited, and may be appropriately selected based on the daily intake or dose according to the dosage form. For example, the content is preferably $1\times10^6$ to $1\times10^{12}$ cfu/g or $1\times10^6$ to $1\times10^{12}$ cfu/mL, more preferably $1\times10^7$ to $1\times10^{11}$ cfu/g or $1\times10^7$ to $1\times10^{11}$ cfu/mL, still more preferably $1\times10^8$ to $1\times10^{10}$ cfu/g or $1\times10^8$ to $1\times10^{10}$ cfu/mL. The unit cfu is an abbreviation of colony forming units, and represents a unit of formation of colonies. In cases where the bacterium is a dead bacterium, cfu/g or cfu/mL can be replaced by cells/g or cells/mL.

The dose of the drug of the present invention for improving a mental health disfunction, in terms of the amount of the bacterium belonging to *Bifidobacterium longum* subsp. *infantis* per kg body weight of the subject to whom the drug is to be administered, is preferably $1\times10^6$ to $1\times10^{12}$ cfu/day, more preferably $1\times10^7$ to $1\times10^{11}$ cfu/day, still more preferably $1\times10^8$ to $1\times10^{10}$ cfu/day. In cases where the bacterium is a dead bacterium, cfu/day can be replaced by cells/day. The administration method for the drug of the present invention for improving a mental health disfunction may be either oral administration or parenteral administration. The drug of the present invention for improving a mental health disfunction may be administered once daily, or dividedly several times daily.

As the formulation carrier, an organic or inorganic carrier may be used according to the dosage form. Examples of carriers for cases of a solid formulation include excipients, binders, disintegrators, lubricants, stabilizers, and correctives.

Examples of the excipients include sugar derivatives such as lactose, saccharose, glucose, mannitol, and sorbitol; starch derivatives such as corn starch, potato starch, α-starch, dextrin, and carboxymethyl starch; cellulose derivatives such as crystalline cellulose, hydroxypropyl cellulose, hydroxypropyl methylcellulose, carboxymethyl cellulose, and carboxymethyl cellulose calcium; gum arabic; dextran; pullulan; silicate derivatives such as light anhydrous silicic acid, synthetic aluminum silicate, and magnesium aluminometasilicate; phosphate derivatives such as calcium phosphate; carbonate derivatives such as calcium carbonate; and sulfate derivatives such as calcium sulfate.

Examples of the binders include, in addition to the above excipients, gelatin; polyvinyl pyrrolidone; and macrogol.

Examples of the disintegrators include, in addition to the above excipients, chemically modified starches such as croscarmellose sodium, sodium carboxymethyl starch, and cross-linked polyvinyl pyrrolidone; and cellulose derivatives.

Examples of the lubricants include talc; stearic acid; metal stearates such as calcium stearate and magnesium stearate; colloidal silica; waxes such as Peegum and spermaceti; boric acid; glycol; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicic acids such as anhydrous silicic acid and silicic acid hydrate; and starch derivatives.

Examples of the stabilizers include p-oxybenzoic acid esters such as methylparaben and propylparaben; alcohols such as chlorobutanol, benzyl alcohol, and phenylethyl alcohol; benzalkonium chloride; acetic anhydride; and sorbic acid.

Examples of the correctives include sweeteners, acidulants, and perfumes. Examples of the carrier used in cases of a liquid for oral administration include solvents such as water; and correctives.

The drug of the present invention for improving a mental health disfunction can be applied to diseases that can be alleviated, prevented, or treated by improvement of a mental health disfunction. The diseases that can be alleviated, prevented, or treated by improvement of a mental health disfunction are diseases the symptoms of which can be determined to have been alleviated or improved when the score(s) of "mental health (MH)" and/or "mental component summary (MCS)" according to SF-36 is increased. Specific examples of such diseases include post-traumatic stress disorder (PTSD), dripping faucet syndrome, alcohol dependence, dissociative disorder, obsessive-compulsive disorder, autonomic imbalance, adjustment disorder, phobic neurosis, anthropophobia, agoraphobia, emotional disorder, tic disorder, personality disorder, and developmental disorder.

Among these diseases, the present invention is especially suitable for diseases caused by suffering from natural disasters.

The drug of the present invention for improving a mental health disfunction may be administered alone, or may be used in combination with another drug such as another mental health disfunction-improving drug, antipsychotic drug, antianxiety drug, hallucinogenic drug, mood stabilizer, mental stimulant, or hypnotic drug.

<Food or Drink Composition>

The food or drink composition of the present invention for improving a mental health disfunction may be produced by adding a bacterium belonging to *Bifidobacterium longum* subsp. *infantis* to a known food or drink, or a novel food or drink composition may be produced by mixing the bacterium with a raw material of a food or drink.

The food or drink composition of the present invention for improving a mental health disfunction may be in any form such as a liquid, paste, solid, or powder. Examples of the composition include tablet confectionery, liquid diets, and feeds including those for pets, and also include flour products, instant foods, processed agricultural products, processed fishery products, processed livestock products, milk and dairy products, fats and oils, basic seasonings, composite seasonings and foods, frozen foods, confectionery, drinks, and other commercially available products.

The food or drink composition for improving a mental health disfunction defined in the present invention can be provided and sold as a food or drink with a label indicating health uses such as a use for improvement of a mental health disfunction.

The act of "labeling" includes any act for informing the intended uses to consumers, and any expression that allows the consumers to assume or infer the intended uses corresponds to the act of "labeling" in the present invention irrespective of, for example, the purpose of the label, the content of the label, and to what object or medium the label is applied.

The "labeling" is preferably carried out with an expression with which the consumers are capable of directly recognizing the intended uses. More specifically, examples of the act of labeling include acts of transfer of, delivery of, displaying for transfer or delivery of, or import of, a food- or drink-related product or packaging of the product on which the intended uses are described, and acts of describing the intended uses in an advertisement, price list, or transaction document related to the product, and displaying or distributing it, or describing the intended uses in information including such a content and providing the information by an electromagnetic method (internet or the like).

On the other hand, regarding the content of the label, the label is preferably a label approved by the government or the like (for example, a label with approval based on a system(s) established by the government, which label is applied in a mode in accordance with the approval). It is preferred to apply such a content of the label to packaging, containers, catalogs, pamphlets, advertisement materials in sales locations such as POPs, or other documents.

Examples of the "label" also include labels for health foods, functional foods, enteral foods, special purpose foods, foods with health claims, foods for specified health uses, foods with nutrient function claims, foods with function claims, quasi drugs, and the like. Particular examples among these include labels approved by the Consumer Affairs Agency, such as labels approved based on a system concerning foods for specified health uses, foods with nutrient function claims, or foods with function claims, or based on a system similar thereto. Specifically, examples of the labels include labels for foods for specified health uses, labels for qualified foods for specified health uses, labels informing that a structure or a function of the body may be influenced, labels informing reduction of a disease risk, and labels informing functionality according to a scientific basis. More specifically, typical examples of the labels include labels for foods for specified health uses (in particular, labels indicating health uses) as specified in a cabinet office order concerning labeling permission for special uses prescribed in the health promotion law (Cabinet Office Order No. 57; Aug. 31, 2009), and labels similar thereto.

The content of the bacterium belonging to *Bifidobacterium longum* subsp. *infantis* in the production of the food or drink composition of the present invention for improving a mental health disfunction is not limited, and may be appropriately selected based on the daily intake. For example, the content is preferably $1 \times 10^6$ to $1 \times 10^{12}$ cfu/g or $1 \times 10^6$ to $1 \times 10^{12}$ cfu/mL, more preferably $1 \times 10^7$ to $1 \times 10^{11}$ cfu/g or $1 \times 10^7$ to $1 \times 10^{11}$ cfu/mL, still more preferably $1 \times 10^8$ to $1 \times 10^{10}$ cfu/g or $1 \times 10^8$ to $1 \times 10^{10}$ cfu/mL. In cases where the bacterium is a dead bacterium, cfu/g or cfu/mL can be replaced by cells/g or cells/mL.

The intake of the food or drink composition of the present invention for improving a mental health disfunction, in terms of the amount of the bacterium belonging to *Bifidobacterium longum* subsp. *infantis* per kg body weight of the subject who takes the composition, is preferably $1 \times 10^6$ to $1 \times 10^{12}$ cfu/day, more preferably $1 \times 10^7$ to $1 \times 10^{11}$ cfu/day, still more preferably $1 \times 10^8$ to $1 \times 10^{10}$ cfu/day. In cases where the bacterium is a dead bacterium, cfu/day can be replaced by cells/day.

The present invention can also employ the following constitutions:

[1] An agent for improving a mental health disfunction or a composition for improving a mental health disfunction, or a food or drink composition for improving a mental health disfunction, comprising as an active ingredient a bacterium belonging to *Bifidobacterium longum* subsp. *infantis*.

[2] The agent for improving a mental health disfunction or the composition for improving a mental health disfunction, or the food or drink composition for improving a mental health disfunction according to [1], wherein the bacterium is *Bifidobacterium longum* subsp. *infantis* BCCM LMG23728.

[3] The agent for improving a mental health disfunction or the composition for improving a mental health disfunction, or the food or drink composition for improving a mental health disfunction according to [1] or [2], wherein the mental health disfunction is evaluated according to SF-36.

[4] The agent for improving a mental health disfunction or the composition for improving a mental health disfunction, or the food or drink composition for improving a mental health disfunction according to [3], wherein the mental health disfunction is a state with a low score(s) of mental health (MH) and/or mental component summary (MCS).

[5] The agent for improving a mental health disfunction or the composition for improving a mental health disfunction, or the food or drink composition for improving a mental health disfunction according to any one of [1] to [4], wherein the improvement of the mental health disfunction is alleviation, improvement, or resolution of a nervous psychological state, depressed mood, or melancholic mood, or enhancement of a mild mood or a pleasant mood.

[6] Use of a bacterium belonging to *Bifidobacterium longum* subsp. *infantis* in production of a composition for improving a mental health disfunction or a mental health disfunction-improving drug.

[7] Use of a bacterium belonging to *Bifidobacterium longum* subsp. *infantis* for improvement of a mental health disfunction.

[8] A bacterium belonging to *Bifidobacterium longum* subsp. *infantis* to be used for improvement of a mental health disfunction.

[9] A method of improving a mental health disfunction, comprising a step of administering a bacterium belonging to *Bifidobacterium longum* subsp. *infantis*, or the agent for improving a mental health disfunction or the composition for improving a mental health disfunction, or the food or drink composition for improving a mental health disfunction according to any one of [1] to [5], to a subject.

[10] A method of alleviation, prevention, or treatment of a disease that can be alleviated, prevented, or treated by improvement of a mental health disfunction, comprising a step of administering a bacterium belonging to *Bifidobacterium longum* subsp. *infantis*, or the agent for improving a mental health disfunction or the composition for improving a mental health disfunction, or the food or drink composition for improving a mental health disfunction according to any one of [1] to [5], to a subject.

[11] An agent for controlling a component ratio of enteric bacteria or a composition for controlling a component ratio of enteric bacteria in an intestinal flora; an agent for improving a component ratio of enteric bacteria or a composition for improving a component ratio of enteric bacteria in an intestinal flora; or a food or drink composition for controlling a component ratio of enteric bacteria in an intestinal flora, or a food or drink composition for improving a component ratio of enteric bacteria in an intestinal flora; comprising as an active ingredient a bacterium belonging to *Bifidobacterium longum* subsp. *infantis*.

[12] The agent for controlling a component ratio of enteric bacteria or the composition for controlling a component ratio of enteric bacteria in an intestinal flora; the agent for improving a component ratio of enteric bacteria or the composition for improving a component ratio of enteric bacteria in an intestinal flora; or the food or drink composition for controlling a component ratio of enteric bacteria in an intestinal flora, or the food or drink composition for improving a component ratio of enteric bacteria in an intestinal flora; according to [11], wherein the ratio of enteric bacteria is a component ratio of bacteria belonging to phylum Firmicutes to bacteria belonging to phylum Bacteroidetes in the intestinal flora.

[13] The agent for controlling a component ratio of enteric bacteria or the composition for controlling a component ratio of enteric bacteria in an intestinal flora; the agent for improving a component ratio of enteric bacteria or the composition for improving a component ratio of enteric bacteria in an intestinal flora; or the food or drink composition for controlling a component ratio of enteric bacteria in an intestinal flora, or the food or drink composition for improving a component ratio of enteric bacteria in an intestinal flora; according to [11] or [12], which reduces the component ratio of bacteria belonging to phylum Firmicutes to bacteria belonging to phylum Bacteroidetes in the intestinal flora.

[14] The agent for controlling a component ratio of enteric bacteria or the composition for controlling a component ratio of enteric bacteria in an intestinal flora; the agent for improving a component ratio of enteric bacteria or the composition for improving a component ratio of enteric bacteria in an intestinal flora; or the food or drink composition for controlling a component ratio of enteric bacteria in an intestinal flora, or the food or drink composition for improving a component ratio of enteric bacteria in an intestinal flora; according to any one of [11] to [13], which increases the occupancy of bacteria belonging to phylum Bacteroidetes in the intestinal flora.

[15] The agent for controlling a component ratio of enteric bacteria or the composition for controlling a component ratio of enteric bacteria in an intestinal flora; the agent for improving a component ratio of enteric bacteria or the composition for improving a component ratio of enteric bacteria in an intestinal flora; or the food or drink composition for controlling a component ratio of enteric bacteria in an intestinal flora, or the food or drink composition for improving a component ratio of enteric bacteria in an intestinal flora; according to any one of [11] to [14], which reduces the occupancy of bacteria belonging to phylum Firmicutes in the intestinal flora.

[16] The agent for controlling a component ratio of enteric bacteria or the composition for controlling a component ratio of enteric bacteria in an intestinal flora; the agent for improving a component ratio of enteric bacteria or the composition for improving a component ratio of enteric bacteria in an intestinal flora; or the food or drink composition for controlling a component ratio of enteric bacteria in an intestinal flora, or the food or drink composition for improving a component ratio of enteric bacteria in an intestinal flora; according to anyone of [11] to [15], wherein the bacterium belonging to *Bifidobacterium longum* subsp. *infantis* is BCCM LMG23728.

EXAMPLES

The present invention is described below in more detail by way of Examples. However, the present invention is not limited to these Examples.

Example 1

(1) Sample Preparation

A culture liquid of *Bifidobacterium longum* subsp. *infantis* BCCM LMG23728 was concentrated and freeze-dried, followed by mixing with maltodextrin manufactured by Matsutani Chemical Industry Co., Ltd., to prepare a bacterial powder comprising *Bifidobacterium longum* subsp. *infantis* BCCM LMG23728. By aliquoting 1.0 g of the bacterial powder into aluminum bags to obtain individual packages each containing $1.0 \times 10^9$ cfu of *Bifidobacterium longum* subsp. *infantis* BCCM LMG23728.

(2) Oral Ingestion Test

For 31 victims of a flood that occurred in the Kelantan district, Malaysia, a test was carried out to investigate the effect of the agent of the present invention for improving a mental health disfunction. Among the 31 individuals, 11 individuals were grouped into an ingestion group, in which one package of the bacterial powder produced in the "(1) Sample Preparation" was ingested once daily for three months. On the other hand, the remaining 20 individuals, who had not been grouped into the ingestion group, out of the 31 subjects were grouped into a non-ingestion group (control group). For each of the ingestion group and the non-ingestion group, QOL was evaluated according to SF-36® (version 2) a total of two times—on the first day of the test (first test), and on the last day of the test (second test), which was three months after the beginning of the test. Based on the method according to "The Journal of Japanese Society of Lumbar Spine Disorders, vol. 8(1), pp. 38-43, 2002", eight items, more specifically, the physical functioning (PF), role physical (RP), bodily pain (BP), general health perception (GH), vitality (VT), social functioning (SF), role emotional (RE), and mental health (MH), were categorized into two groups, more specifically, into physical component items and mental component items, and the physical component summary (PCS) and the mental component summary (MCS) were calculated using SF-36® (version 2), followed by testing statistically significant differences using the Mann-Whitney U test.

(3) Results

For each of the eight items according to SF-36, more specifically, the physical functioning (PF), role physical (RP), bodily pain (BP), general health perception (GH), vitality (VT), social functioning (SF), role emotional (RE), and mental health (MH), and also the physical component summary (PCS) and the mental component summary (MCS), the score on the last day of the test and the variation value of scores between before and after the test, that is the value obtained by subtracting the score on the first day of the test from the score on the last day of the test, were calculated. The results were as shown in Table 1.

TABLE 1

|  | Score on the last day of the test | | Variation value of scores between before and after the test | |
| --- | --- | --- | --- | --- |
|  | Non-ingestion group | Ingestion group | Non-ingestion group | Ingestion group |
| Physical functioning (PF) | 76.3 ± 23.2 | 73.6 ± 32.7 | −0.25 ± 22.03 | 21.36 ± 49.70 |
| Role physical (RP) | 81.1 ± 44.0 | 72.7 ± 46.7 | 5.60 ± 45.67 | −6.82 ± 50.11 |
| Bodily pain (BP) | 85.0 ± 23.6 | 82.5 ± 18.7 | 2.55 ± 23.06 | 15.09 ± 18.32 |
| General health perception (GH) | 67.4 ± 14.8 | 66.4 ± 14.3 | −1.85 ± 17.15 | 5.91 ± 14.46 |
| Vitality (VT) | 66.5 ± 21.3 | 72.7 ± 17.8 | −6.50 ± 24.28 | 6.82 ± 19.01 |
| Social functioning (SF) | 86.4 ± 18.0 | 83.2 ± 17.8 | 4.30 ± 34.86 | 10.00 ± 18.08 |
| Role emotional (RE) | 83.4 ± 36.7 | 91.8 ± 27.1 | −6.70 ± 42.72 | 13.09 ± 36.24 |
| Mental health (MH) | 67.0 ± 24.8 | 80.4 ± 29.0* | −13.40 ± 28.97 | 17.27 ± 34.48** |
| Physical component summary (PCS) | 50.3 ± 7.7 | 47.3 ± 8.9 | 0.99 ± 5.63 | 2.17 ± 9.07 |
| Mental component summary (MCS) | 49.8 ± 10.4 | 56.8 ± 6.5* | −4.44 ± 12.35 | 7.92 ± 9.64* |

Figure 2:
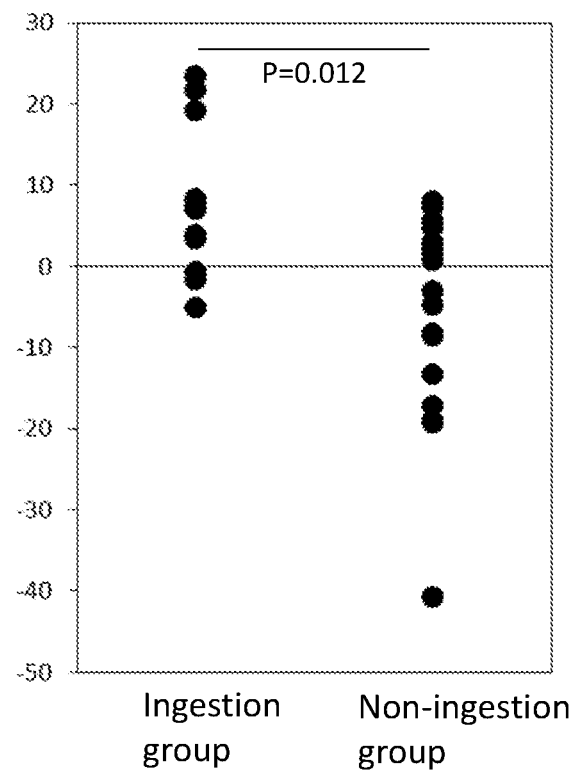
FIG. 2 shows a diagram illustrating changes in the "mental component summary, MCS" score according to SF-36 for a group who ingested *Bifidobacterium longum* subsp. *infantis* BCCM LMG23728 and a group who did not ingest it.

Each score is represented as average ± standard deviation.
*P < 0.05; VS non-ingestion group, Mann-Whitney U-test
P < 0.01; VS non-ingestion group, Mann-Whitney U-test Among the eight items of SF-36, seven items, more specifically, the physical functioning (PF), role physical (RP), bodily pain (BP), general health perception (GH), vitality (VT), social functioning (SF), and role emotional (RE), and also the physical component summary (PCS), showed no significant difference between the non-ingestion group and the ingestion group for neither the score on the last day of the test nor the variation value of scores between before and after the test. On the other hand, regarding each of the mental health (MH) and the mental component summary (MCS), the variation value of scores between before and after the test was as shown in FIG. 1 and FIG. 2**, wherein the ingestion group showed significantly higher values than the non-ingestion group. More specifically, the variation value of scores (average) of the mental health (MH) was 17.27 in the ingestion group, indicating an increase in the score, whereas that was −13.40 in the non-ingestion group, indicating a decrease in the score in contrast to the ingestion group. Similarly, the variation value of scores (average) of the mental component summary (MCS) was 7.92 in the ingestion group, indicating an increase in the score, whereas that was −4.44 in the non-ingestion group, indicating a decrease in the score.

Figure 3:
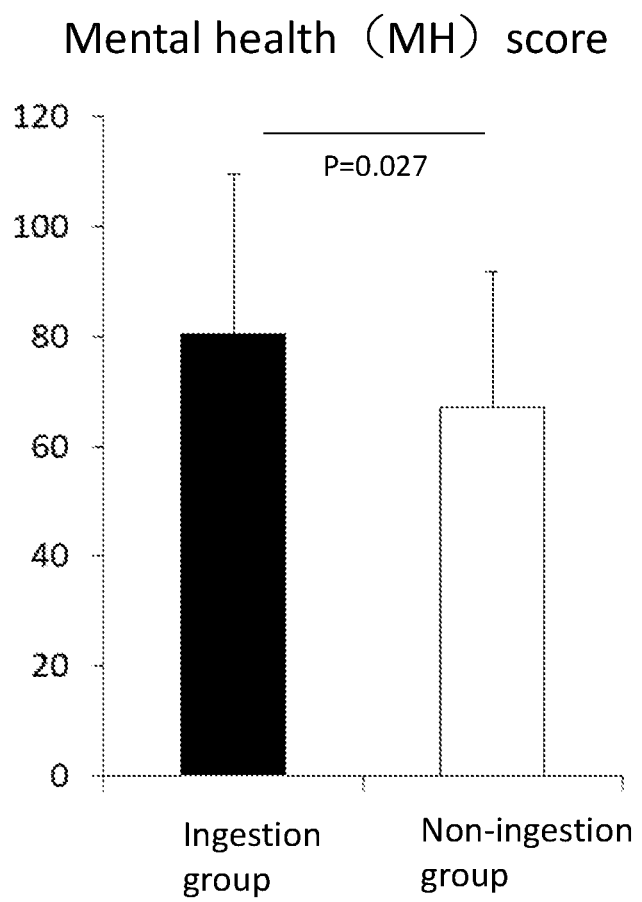
FIG. 3 shows a diagram illustrating the "mental health (MH)" score according to SF-36 for a group who ingested *Bifidobacterium longum* subsp. *infantis* BCCM LMG23728 and a group who did not ingest it on the last day of each test.
Figure 4:
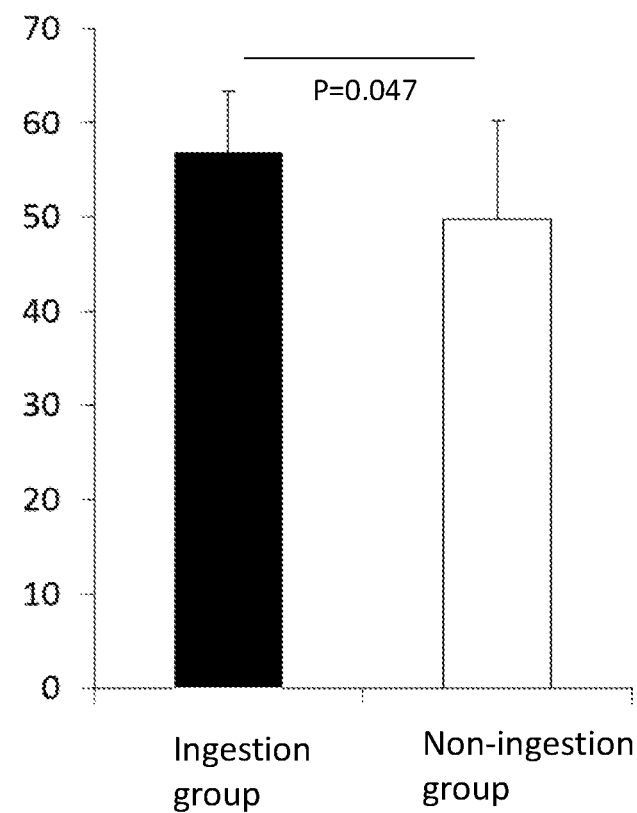
FIG. 4 shows a diagram illustrating the "mental component summary, MCS" score according to SF-36 for a group who ingested *Bifidobacterium longum* subsp. *infantis* BCCM LMG23728 and a group who did not ingest it on the last day of each test.

Further, as shown in FIG. 3 and FIG. 4, the scores of the mental health (MH) and the mental component summary (MCS) on the last day of the test were significantly higher in the ingestion group than in the non-ingestion group. More specifically, while the score (average) of the mental health (MH) on the last day of the test was 80.4 in the ingestion group, it was 67.0 in the non-ingestion group, so that the score in the non-ingestion group was lower than that in the ingestion group by 10 points or more. Further, while the score (average) of the mental component summary (MCS) on the last day of the test was 56.8 in the ingestion group, it was 49.8 in the non-ingestion group, so that the score in the non-ingestion group was lower than that in the ingestion group by 7 points.

From the results of the present test, it became clear that ingestion of a bacterial powder of *Bifidobacterium longum* subsp. *infantis* BCCM LMG23728 increases the scores of the mental health (MH) and the mental component summary (MCS) according to SF-36. In mental diseases such as depression, the eight items of SF-36 are generally low, so that it can be assumed that the SF-36 scores generally increase when mental diseases such as depression are improved. In the present test, however, only the scores of the mental health (MH) and the mental component summary (MCS) according to SF-36 significantly increased. Thus, it has been confirmed that scores of the mental health (MH) and the mental component summary (MCS) increased and a mental health disfunction improved by ingestion of the bacterial powder of *Bifidobacterium longum* subsp. *infantis* BCCM LMG23728.

Example 2

(1) Analysis of Intestinal Flora

In order to study association between the effect of improving a mental health disfunction found in Example 1 and the intestinal flora (brain-gut interaction), analysis of the intestinal flora was carried out for the subjects of Example 1. More specifically, feces were collected on the last day of the test from the non-ingestion group and the ingestion group of Example 1, and each collected fecal sample was suspended in RNA-Later manufactured by Thermo Fisher Scientific Inc. and stored at normal temperature. From the stored solution, DNA of bacteria contained in the feces was extracted using a Qiagen stool DNA extraction kit, manufactured by QIAGEN, to obtain a DNA solution.

Subsequently, in order to amplify the third to fourth variable regions of the 16S rRNA gene of the bacteria, Tru357F (5'-CGCTCTTCCGATCTCTGTACG-GRAGGCAGCAG-3'; SEQ ID NO:1) and Tru806R (5'-CGCTCTTCCGATCTGACGGAC-TACHVGGGTWTCTAAT-3'; SEQ ID NO:2) as the 1st primer set, and Fwd (5'-AATGATACGGCGACCACCGAGATCTA-CACNNNNNNNNNACACTCTTTCCCTACAC GACGCTCTTCCGATCTCTG-3'; SEQ ID NO:3) and Rev (5'-CAAGCAGAAGACGGCAT-ACGAGATNNNNNNNNNGTGACTGGAGTTCA-GACGTGTG CTCTTCCGATCTGAC-3'; SEQ ID NO:4) as the 2nd primer set required for analysis using a next-generation sequencer Miseq (manufactured by Illumina, Inc.) were designed, and the primers were synthesized by the oligo primer preparation service by Life Technologies. The "N"s in the base sequences represent bar code sequences composing of arbitrary bases.

A total of 25 μL of a reaction solution containing the DNA solution and the 1st primer set was prepared using a Takara Extaq HS kit manufactured by Takara Bio Inc. Nucleic acid amplification reaction was carried out using a thermal cycler. PCR reaction was carried out as follows: 94° C.—3 minutes; 30 cycles of 94° C.—30 seconds, 50° C.—30 seconds, and 72° C.—30 seconds; and then 72° C.—5 minutes.

Subsequently, PCR reaction was carried out under the same conditions as in the case using the 1st primers, except that 1 μL of the resulting PCR product was used as a template, the 2nd primer set was used and that the number of cycles was 8. The resulting PCR product was purified using a QIA quick 96 PCR Purification kit manufactured by QIAGEN. A mixture prepared by mixing PCR products derived from a plurality of samples at the same concentration was subjected to a Miseq v3 Reagent kit manufactured by Illumina, Inc., and sequencing analysis was carried out with Miseq.

From the paired-end sequences obtained by the sequencing analysis, sequences corresponding to Reference Consortium human build 38 and PhiX 174 were detected using bowtie-2 (ver. 2-2.2.4), and the detected sequences were excluded from the analysis. Thereafter, base sequences with a PHRED quality score of 17 or less were trimmed. Regarding each of the sequences shorter than 150 bases and the sequences whose average PHRED quality score for the entire sequence was 25 or less, deletion of the entire sequence was carried out. Thereafter, the paired-end sequences were combined using fastq-join (ver. 1.1.2-537), and chimeric sequences were removed using USEARCH (ver. 5.2.32) and the gold database (http://drive5.com/otu-pipe/gold.tz), to obtain sequences to be used for the analysis. The analysis of bacteria was carried out using the open-reference OTU (Operational Taxonomy Unit) picking method in the Qiime software (version 1.8.0) and the database: Greengenes database13_8, wherein each OTU included sequences having a homology of 97%. Representative sequences of the OTUs were subjected to homology search against the database: Greengenes database13_8 to analyze the component ratios of enteric bacteria.

(2) Results

Figure 5:
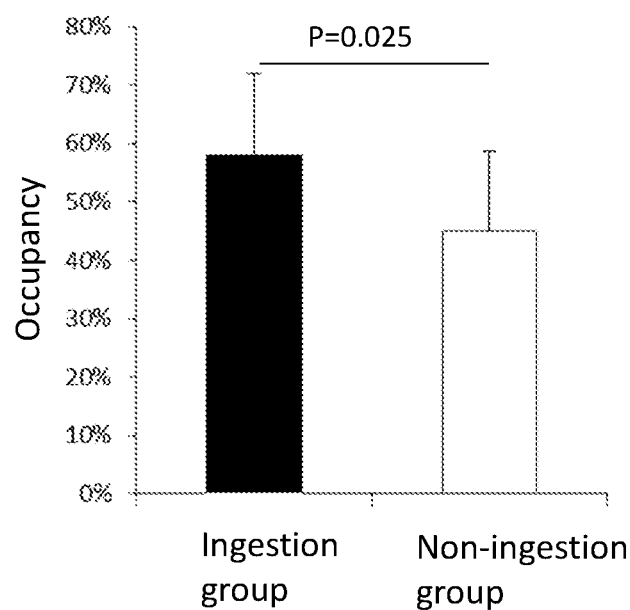
FIG. 5 shows a diagram illustrating the occupancy of bacteria belonging to the phylum Bacteroidetes in the intestinal flora for a group who ingested *Bifidobacterium longum* subsp. *infantis* BCCM LMG23728 and a group who did not ingest it after completion of the test.
Figure 6:
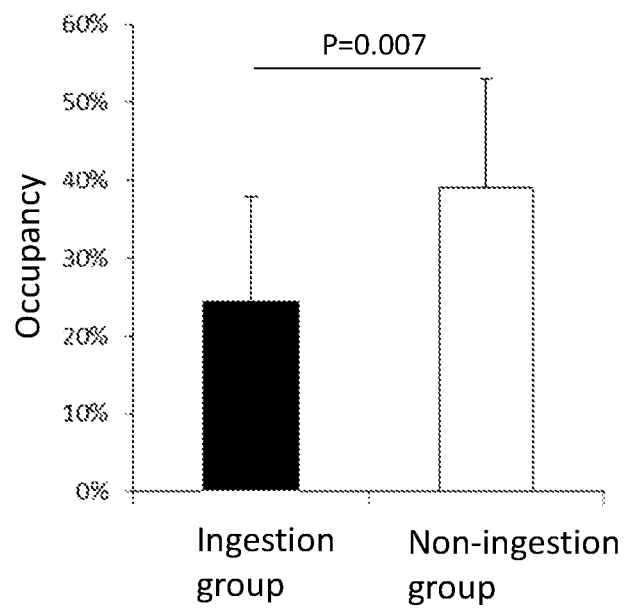
FIG. 6 shows a diagram illustrating the occupancy of bacteria belonging to the phylum Firmicutes in the intestinal flora for a group who ingested *Bifidobacterium longum* subsp. *infantis* BCCM LMG23728 and a group who did not ingest it after completion of the test.
Figure 7:
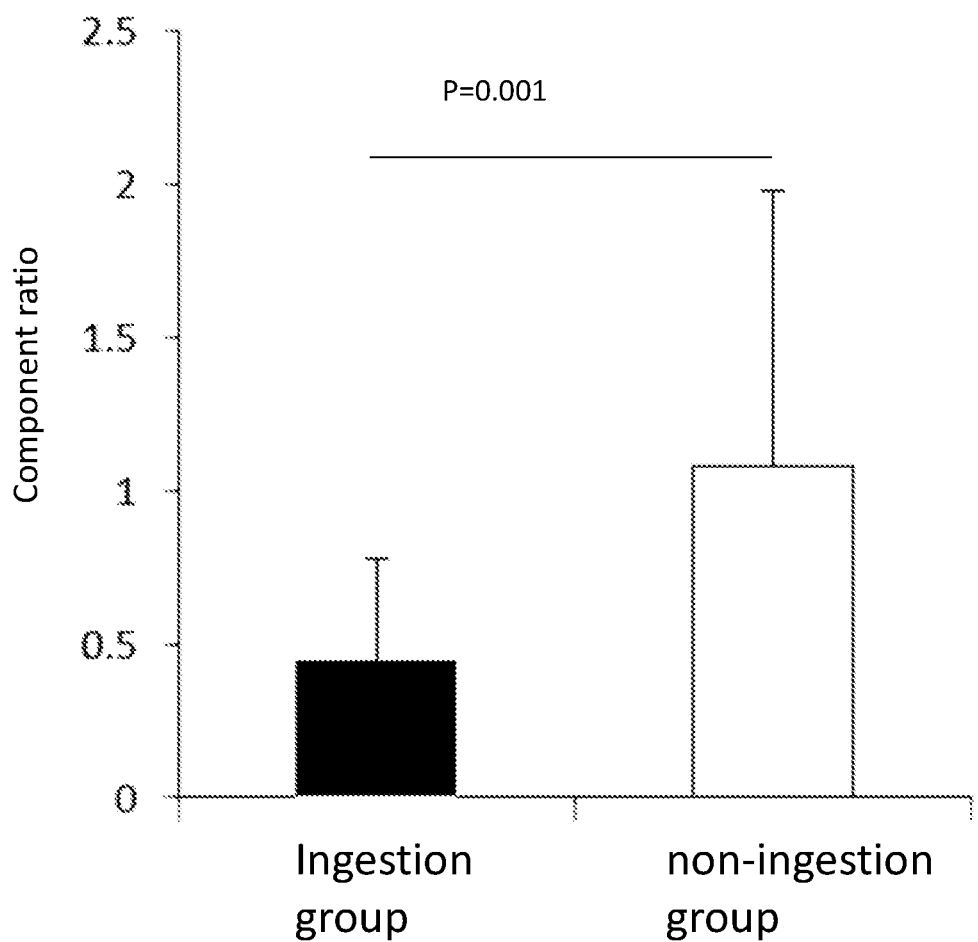
FIG. 7 shows a diagram illustrating the component ratio of bacteria belonging to the phylum Firmicutes to bacteria belonging to the phylum Bacteroidetes, that is the occupancy of bacteria belonging to the phylum Firmicutes/the occupancy of bacteria belonging to the phylum Bacteroidetes, in the intestinal flora for a group who ingested *Bifidobacterium longum* subsp. *infantis* BCCM LMG23728 and a group who did not ingest it after completion of each test.

As shown in FIGS. 5, 6, and 7, after the test, the occupancy of bacteria belonging to the phylum Bacteroidetes in the intestinal flora in the ingestion group was 58% on average. This was a significantly higher value compared to the occupancy of bacteria belonging to the phylum Bacteroidetes in the non-ingestion group, which was 45% on average (FIG. 5). Further, after the test, the occupancy of bacteria belonging to phylum Firmicutes in the intestinal flora in the ingestion group was 24% on average. This was a significantly lower value compared to the occupancy of bacteria belonging to the phylum Firmicutes in the non-ingestion group, which was 39% on average (FIG. 6). Further, after the test, the component ratio between the two bacteria in the intestinal flora in the ingestion group (bacteria belonging to the phylum Firmicutes/bacteria belonging to the phylum Bacteroidetes) was 0.44 on average. This was a significantly lower value compared to the component ratio between the two bacteria in the non-ingestion group, which was 1.08 on average (FIG. 7). The significant differences were tested using the Mann-Whitney U test.

Figure 8:
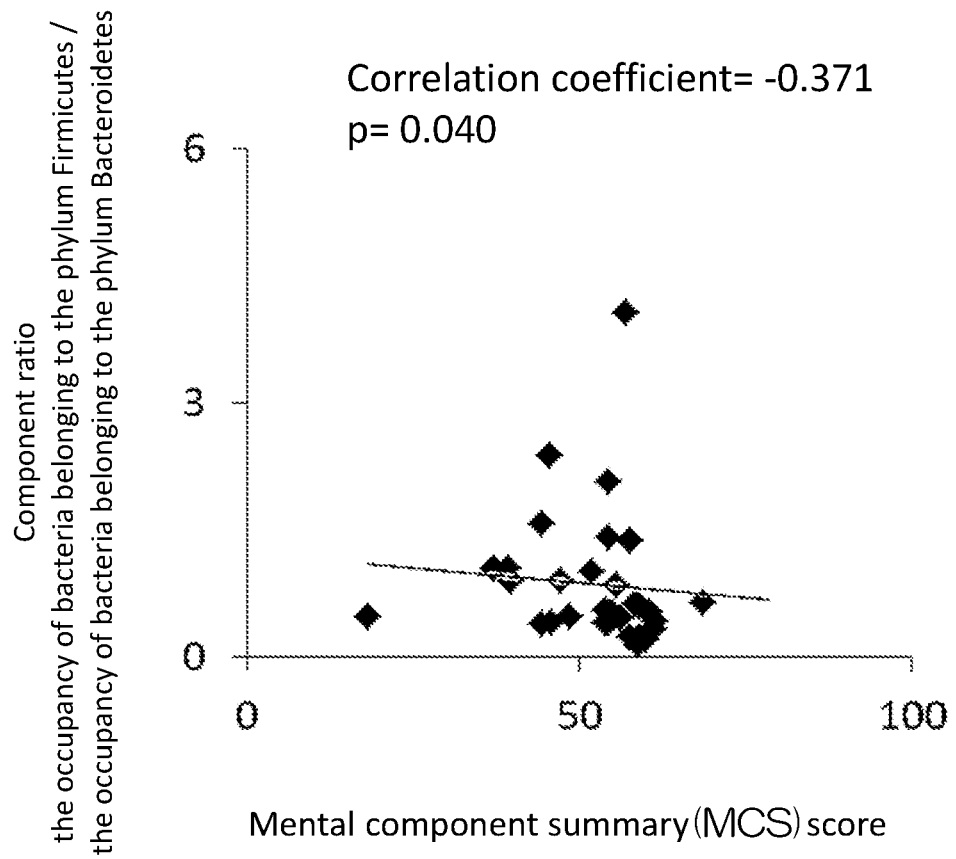
FIG. 8 shows a diagram illustrating a correlation between the "mental component summary, MCS" score according to SF-36 and the component ratio of bacteria belonging to the phylum Firmicutes to bacteria belonging to the phylum Bacteroidetes, that is the occupancy of bacteria belonging to the phylum Firmicutes/the occupancy of bacteria belonging to the phylum Bacteroidetes, in the intestinal flora for a group who ingested *Bifidobacterium longum* subsp. *infantis* BCCM LMG23728.

Spearman's correlation between the mental component summary (MCS) after the test in Example 1 shown in FIG. 4 and the component ratio in the intestinal flora shown in FIG. 7 was analyzed using IBM SPSS Statistics (Ver. 22). As a result, as shown in FIG. 8, a significant negative correlation was found between them. In other words, a correlation was found between the increase in the mental component summary (MCS) and the decrease in the component ratio in the intestinal flora due to the ingestion of *Bifidobacterium longum* subsp. *infantis* BCCM LMG23728. It was thus suggested that *Bifidobacterium longum* subsp. *infantis* BCCM LMG23728 can improve a mental health disfunction by decreasing the component ratio in the intestinal flora of subject who ingest it.

Preparation Example 1

To 3 mL of MRS liquid medium, *Bifidobacterium longum* subsp. *infantis* BCCM LMG23728 is added, and anaerobic culture is carried out at 37° C. for 16 hours. The resultant culture liquid is then concentrated and freeze-dried to obtain a bacterial powder of the bacterium. The resultant bacterial powder is mixed as appropriate with an excipient and/or the like to prepare tablets. The resultant tablets are ingested every day for three months such that the intake of the bacterium is $1\times10^6$ to $1\times10^{12}$ cfu/kg body weight/day.

By the ingestion of the tablets, an effect of improving a mental health disfunction, an effect of improving intestinal flora component ratio and an effect of improving intestinal flora component ratio can be expected.

Preparation Example 2

To 3 mL of MRS liquid medium, *Bifidobacterium longum* subsp. *infantis* BCCM LMG23728 is added, and anaerobic culture is carried out at 37° C. for 16 hours. The resultant culture liquid is then concentrated and freeze-dried to obtain a bacterial powder of the bacterium. The resultant bacterial powder is added to a fermented-milk raw material to obtain a fermented milk. The resultant fermented milk is ingested every day for at least three months such that the intake of the bacterium is $1\times10^6$ to $1\times10^{12}$ cfu/kg body weight/day.

By the ingestion of the fermented milk, an effect of improving a mental health disfunction, an effect of controlling intestinal flora component ratio and an effect of improving intestinal flora component ratio can be expected.

The invention claimed is:

1. A method of improving a mental health disfunction, comprising administering a bacterium in an effective amount to a subject in need thereof,
wherein the mental health disfunction is mental health (MH) and/or mental component summary (MCS) which are/is evaluated according to SF-36®, and
wherein the bacterium is *Bifidobacterium longum* subsp. *infantis* BCCM LMG23728 or *Bifidobacterium longum* subsp. *infantis* M-63 (NITE BP-02623).

2. The method according to claim 1, wherein the mental health disfunction is one with a MH score of 70 or less and/or MCS score of 50 or less.

3. The method according to claim 1, wherein the bacterium is an active ingredient in a composition.

* * * * *

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: primer 1

<400> SEQUENCE: 1
cgctcttccg atctctgtac ggraggcagc ag                                     32

<210> SEQ ID NO 2
<211> LENGTH: 37
<212> TYPE: DNA
<213> ORGANISM: Artificial Sequence
<220> FEATURE:
<223> OTHER INFORMATION: primer 2

<400> SEQUENCE: 2
cgctcttccg atctgacgga ctachvgggt wtctaat                                37

<210> SEQ ID NO 3
<211> LENGTH: 73
<212> TYPE: DNA
<213> ORGANISM: Artificial Sequence
<220> FEATURE:
<223> OTHER INFORMATION: primer 3
<220> FEATURE:
<221> NAME/KEY: misc_feature
<222> LOCATION: (30)..(37)
<223> OTHER INFORMATION: n is a, c, g, or t

<400> SEQUENCE: 3
```

```
aatgatacgg cgaccaccga gatctacacn nnnnnnnaca ctctttccct acacgacgct    60
cttccgatct ctg                                                       73

<210> SEQ ID NO 4
<211> LENGTH: 69
<212> TYPE: DNA
<213> ORGANISM: Artificial Sequence
<220> FEATURE:
<223> OTHER INFORMATION: primer 4
<220> FEATURE:
<221> NAME/KEY: misc_feature
<222> LOCATION: (25)..(32)
<223> OTHER INFORMATION: n is a, c, g, or t

<400> SEQUENCE: 4
caagcagaag acggcatacg agatnnnnnn nngtgactgg agttcagacg tgtgctcttc    60
cgatctgac                                                            69
```